(12) United States Patent
Jung et al.

(10) Patent No.: US 10,125,384 B2
(45) Date of Patent: *Nov. 13, 2018

(54) REAGENT COMPOSITION FOR REDOX REACTION

(71) Applicant: I-SENS, INC., Seoul (KR)

(72) Inventors: Sung-Kwon Jung, Incheon (KR); Moon Hwan Kim, Seoul (KR); Eun Hye Im, Incheon (KR); Myeongho Lee, Seoul (KR); Ung Ki Lee, Incheon (KR); Geun Sig Cha, Seoul (KR); Hakhyun Nam, Seoul (KR)

(73) Assignee: I-SENS. INC., Seoul (KR)

( * ) Notice: Subject to any disclaimer, the term of this patent is extended or adjusted under 35 U.S.C. 154(b) by 128 days.

This patent is subject to a terminal disclaimer.

(21) Appl. No.: 14/398,440

(22) PCT Filed: Jan. 25, 2013

(86) PCT No.: PCT/KR2013/000632
§ 371 (c)(1),
(2) Date: Oct. 31, 2014

(87) PCT Pub. No.: WO2013/165076
PCT Pub. Date: Nov. 7, 2013

(65) Prior Publication Data
US 2015/0101929 A1    Apr. 16, 2015

(30) Foreign Application Priority Data

May 2, 2012    (KR) ........................ 10-2012-0046531

(51) Int. Cl.
*C12Q 1/00* (2006.01)
*C12Q 1/26* (2006.01)
(Continued)

(52) U.S. Cl.
CPC ............... *C12Q 1/006* (2013.01); *C12Q 1/26* (2013.01); *G01N 33/5438* (2013.01); *G01N 33/54393* (2013.01); *G01N 27/3272* (2013.01)

(58) Field of Classification Search
CPC .......... C12Q 1/00; C12Q 1/004; C12Q 1/005; C12Q 1/006; C12Q 1/26; C12Q 1/32
See application file for complete search history.

(56) References Cited

U.S. PATENT DOCUMENTS 5,736,406 A    4/1998    Miyauchi et al.
8,083,926 B2    12/2011    Chen
(Continued)

FOREIGN PATENT DOCUMENTS

EP    0992589 A2    4/2000
JP    08-050113 A    2/1996
(Continued)

OTHER PUBLICATIONS

Machine translation of JP 2005-118014; Takama, Toshio; published May 12, 2005; accessed and printed Aug. 11, 2016; pp. 1-15.*
(Continued)

*Primary Examiner* — Edward J. Schmiedel
(74) *Attorney, Agent, or Firm* — McDermott Will & Emery (57) ABSTRACT

The present invention relates to a stabilizing composition useful for improving the stability of reagent for redox reaction, and a reagent composition for redox reaction having an improved stability. The reagent composition for redox reaction can be applied for a reagent for electrochemical biosensor.

14 Claims, 7 Drawing Sheets

(51) Int. Cl.
*G01N 33/543* (2006.01)
*G01N 27/327* (2006.01)

(56) References Cited

U.S. PATENT DOCUMENTS

| | | | |
|---|---|---|---|
| 2001/0021523 A1 | 9/2001 | Hattori et al. | |
| 2004/0217019 A1* | 11/2004 | Cai | C12Q 1/004 205/792 |
| 2008/0035479 A1* | 2/2008 | Liu | C12Q 1/002 204/403.14 |
| 2011/0011739 A1* | 1/2011 | Cui | B01L 3/5027 204/403.1 |
| 2013/0081958 A1* | 4/2013 | Jung | C12Q 1/004 205/777.5 |

FOREIGN PATENT DOCUMENTS

| | | |
|---|---|---|
| JP | 11-051895 | 2/1999 |
| JP | 2000-065777 A | 3/2000 |
| JP | 2000-221157 A | 8/2000 |
| JP | 2005-118014 A | 5/2005 |
| JP | 2006-215034 A | 8/2006 |
| JP | 2010-237145 A | 10/2010 |
| JP | 2014-528573 A | 10/2014 |
| KR | 10-1992-0701476 A | 8/1992 |
| KR | 10-2002-0008941 A | 2/2002 |
| KR | 10-2004-0105429 A | 12/2004 |
| KR | 10-2005-0071474 A | 7/2005 |
| KR | 10-0496753 B1 | 9/2005 |
| KR | 10-2006-0089464 A | 8/2006 |
| KR | 10-0854389 B1 | 8/2008 |
| KR | 10-2008-0080841 A | 9/2008 |
| KR | 10-2008-0084030 A | 9/2008 |
| KR | 10-2008-0088028 A | 10/2008 |
| KR | 10-2013-0035844 A | 4/2013 |
| WO | 90/12889 A1 | 11/1990 |
| WO | WO-01/036955 A1 | 5/2001 |
| WO | WO-2006/096619 A2 | 9/2006 |
| WO | WO 2013048087 A2 * | 4/2013 ............ C12Q 1/004 |

OTHER PUBLICATIONS

Sigma-Aldrich; Ru(NH3)6Cl3—Hexaammineruthenium(III) chloride; accessed and printed Jun. 30, 2017; http://www.sigmaaldrich.com/catalog/product/aldrich/262005?lang=en&region=US.*

Tanaka, et al., "612bis—Thionine and Ferric Chelate Compounds as Coupled Mediators in Microbial Fuel Cells," Bioelectrochemistry and Bioenergetics, 1983, pp. 289-297.

Mendoza et al., Electrochemisty of Encapsulated Guests: Ferrocene inside Cram's Hemicarcerands. Chem. Eur. J. 1998;4(5):864-870.

Podkoscielny et al., Ferrocene derivatives included in a water-soluble cavitand: are they electroinactive? Org Lett. Jul. 3, 2008;10(13):2865-8.

Amine et al., "Characterization of Mediated and Non-Mediated Oxidase Enzyme Based Glassy Carbon Electrodes," Talanta, 0993, vol. 40, No. 8, pp. 1157-1162.

* cited by examiner

thionine
3,7-diamino-5-phenothiazinium

[Fig. 7]

REAGENT COMPOSITION FOR REDOX REACTION

BACKGROUND OF THE INVENTION (a) Field of the Invention

The present invention relates to a stabilizing composition being useful for improving the stability of reagent for redox reaction, and a reagent composition for redox reaction having an improved stability. The reagent composition for redox reaction can be applied for a reagent for electrochemical biosensor.

(b) Description of the Related Art

The periodic measurement of a blood glucose level is important to managing the diabetes, and has been performed by using various electrochemical biosensors with precision and accuracy. The electrochemical biosensor for measuring the blood glucose level is manufactured by applying a reagent including enzyme, electron transfer and various stabilizers and dispersant to the working electrode and drying the working electrode applied with the reagent. The most important factors affecting the characteristics of electrochemical biosensor are the properties of the enzyme and the electron transfer.

For example, FAD-GOx (flavin adenine dinucleotide-glucose oxidase) used for most commercially-available electrochemical sensor as a glucose oxidoreductase has a heat stability and a reaction specificity to oxidize only glucose, but tends to show a large fluctuation in the measured values on the blood sources such as venous blood, arterial blood and peripheral blood, by using the sensor adopting the FAD-GOx, because the enzyme reacts with oxygen dissolved in blood.

Meanwhile, the sensor adopting pyrrole quinolone quinone-glucose dehydrogenase (PQQ-GDH) is not nearly affected by the blood oxygen, but shows the specificity to monosaccharides such as mannose, maltose and lactose, or disaccharides. In particular, it has been reported that the sensor can cause the faculty medical practice due to the influence of maltose in a patient with kidney peritoneal dialysis. The sensor adopting nicotinamide adenine dinucleotide-glucose dehydrogenase (NAD-GDH) shows better reaction specificity than PQQ-GDH, because it does not react with the disaccharides such as mannose, maltose and lactose, but has a disadvantages of need of NAD or NADP as cofactor and a low storage stability.

Recently, the electrochemical sensor using flavin adenine dinucleotide-glucose dehydrogenase (FAD-GDH) has been wildly used, because it is not affected by the amount of blood oxygen, has a high stability and does not have a specificity to maltose unlike PQQ-GDH. However, FAD-GDH can use limited kinds of electron transfers (mediator) according to the kinds of bacteria or fungi producing the enzyme.

Potassium ferricyanide $[K_3Fe(CN)_6]$ is used universally as the electron transfer. It is cheap and is useful for the sensors adopting FAD-GOx, PQQ-GDH or FAD-GDH due to a high reactivity. However, the sensor using Potassium ferricyanide as the electron transfer can show the measurement error caused by an interfering substance such as uric acid or gentisic acid in blood, and must be manufactured and stored with a special caution due to the deterioration caused by the temperature and humidity. In addition, because the ground current changes after being stored in a long time, it has a difficulty in accurate detecting a low concentration of glucose.

Hexaammineruthenium chloride $[Ru(NH_3)_6Cl_3]$ has a better redox stability, compared to ferricyanide. The sensor employing hexaammineruthenium chloride as an electron transfer can be prepared and stored easily and a small change in the ground current after being stored in a long time. However, hexaammineruthenium chloride cannot be used together with FAD-GDH, resulting in the difficulty in manufacturing a commercially-useful sensor.

Recently, there are several attempts to detect the blood glucose by using special types of biosensors which employ the electrode with nanopore surface without including enzyme and electron transfer. For examples, U.S. Pat. No. 8,083,926 presents the method of detecting a low concentration of glucose by using the electrode with cyclodextrin nanopore. The sensor cannot be suitable for detecting a very small amount of glucose, and for mass production of sensor.

Therefore, a reagent for redox reaction, or more specifically a reagent for redox reaction useful for electrochemical biosensor has no affection of oxygen, a small range of performance variation being caused by the temperature, the humidity and the long-term storage, detection of a wide range of glucose concentration, and suitability for mass-production, is still required. The present invention provides a biosensor reagent composition satisfying the requirements.

SUMMARY OF THE INVENTION

The present inventors confirmed that an oxidoreductase and an electron transfer could be stabilized by adding a hydrophilic inclusion compound (inclusion compound) to a reagent for redox reaction useful for an electrochemical biosensor and completed the present invention.

Accordingly, an embodiment of the present invention provides a composition for stabilizing a reagent for redox reaction including hydrophilic inclusion compound.

Another embodiment provides a reagent composition for redox reaction with an improved stability, including oxidoreductase, electron-transfer mediator, and hydrophilic inclusion compound.

Further embodiment provides a method of preparing the reagent composition for redox reaction with an improved stability, including a step of mixing oxidoreductase, electron-transfer mediator, and hydrophilic inclusion compound.

Further embodiment provides an electrochemical biosensor including the reagent composition for redox reaction with an improved stability useful for electrochemical biosensor.

DETAILED DESCRIPTION

The present inventors found that when thionine or 1-Methoxy PMS (1-Methoxy-5-methylphenazinium methylsulfate) is used in combination of hexaammineruthenium chloride as the electron-transfer mediator for FAD-GDH enzyme, the increased reaction rate between the enzyme and the electron transfer improved notably the detection performance for glucose and filed a patent application for a reagent composition useful for a biosensor (Korean patent application number 2012-0009668).

As described in the prior application, the thionine (FIG. 6) and thionine derivatives having the similar structure (FIG. 7) were used together as a second electron-transfer mediator in order to increase the reaction rate of the metal-containing complex such as hexaammineruthenium chloride as a first electron-transfer mediator) and the oxidoreductase with a low reactivity, and thus caused a problem of instability. The present inventors have continuous researches for resolving the instability problem, and found that when a hydrophilic inclusion compound (inclusion compound) such as hydroxypropyl-α-cyclodextrin (HP-α-CD), (hydroxypropyl-β-cyclodextrin (HP-β-CD), or hydroxypropyl-γ-cyclodextrin (HP-γ-CD) was added to the reagent composition as a reagent stabilizer sensor, the oxidoredox reaction efficiency and the performance change of the glucose detection were not nearly detected. The hydrophilic inclusion compound can form an inclusion complex with thionine, thereby increasing the solubility of thionine and can restrict the direct reaction with the enzyme, thereby increasing the stability of the reagent composition. For example, HP-β-CD has a very high water-solubility, such that it can be dissolved in water to 50% (w/v) per unit volume. HP-β-CD can form a complex with a poorly-soluble material, resulting in a stable complex dissolved in water.

The present inventors found that the hydrophilic inclusion compound contained in an electrochemical biosensor including FAD-GDH, hexaammineruthenium and thionine of transfer mediator could be used as a reagent for redox reaction which satisfied the properties of no reaction with oxygen, a very small performance variation caused by the temperature and humidity, no influence of detection sensitivity caused by the interfering substance, and good long-term stability, and that the hydrophilic inclusion compound could be used as a reagent for electrochemical biosensor and a biosensor using the same, thereby completing the present invention.

In accordance with the present invention, the reagent for redox reaction or more specifically the reagent for redox reaction useful for electrochemical biosensor has no affection of oxygen, a small range of performance variation being caused by the temperature, the humidity and the long-term storage, detection of a wide range of glucose concentration (for example, 5 to 1000 mg/dL), and suitability for mass-production.

In another embodiment, the reagent composition is applied for a glucose-detection biosensor as an example, but can be applied for various kinds of biosensor detecting different kinds of substances such as cholesterol, lactate, creatine, hydroperoxide, alcohol, amino acid, and glutamate by changing the used enzyme.

According to the present invention, a stabilizing agent of reagent used for biosensor and a reagent composition including the stabilizing agent have no affection of oxygen and interfering substances, a small range of performance variation being caused by the temperature, the humidity and the long-term storage, and thus can be useful as an electrochemical biosensor detecting various metabolites in blood, specifically glucose.

DETAILED DESCRIPTION OF THE EMBODIMENTS

As described above, an embodiment of the present invention provides a composition for stabilizing a reagent for redox reaction including hydrophilic inclusion compound.

An embodiment of the present invention provides a reagent used for biosensor including hydrophilic inclusion compound, because the reagent for redox reaction can be used for a reagent of electrochemical biosensor.

An embodiment of the present invention provides a reagent composition for redox reaction with increased stability, including oxidoreductase, electron-transfer mediator, and hydrophilic inclusion compound.

An embodiment of the present invention provides a reagent used for biosensor including oxidoreductase, electron-transfer mediator, and hydrophilic inclusion compound, because the reagent for redox reaction can be used for a reagent of electrochemical biosensor.

An embodiment of the present invention provides a method of preparing a reagent for redox reaction including a step of mixing oxidoreductase, electron-transfer mediator and hydrophilic inclusion compound.

An embodiment of the present invention provides a method of preparing a reagent for redox reaction useful for electrochemical biosensor, including a step of mixing oxidoreductase, electron-transfer mediator and hydrophilic inclusion compound, because the reagent for redox reaction can be used for a reagent of electrochemical biosensor.

An embodiment of the present invention provides a electrochemical biosensor including a reagent composition for electrochemical biosensor with increased stability & reagent composition.

The present invention will be explained in more detail hereinafter.

Herein, 'inclusion compound' refers to a clathrate compound or an enclosure compound, and means a complex in which one chemical compound forms a lattice cavity in which molecules of a second compound are fit under a suitable condition.

The hydrophilic inclusion compound can be at least a compound selected from the group consisting of cyclodextrins and its derivatives, more preferably cyclodextrins. The cyclodextrins can reduce the change in glucose detection capability, even if the sensor for detecting glucose is stored in a long time.

The cyclodextrins include α-cyclodextrin of 6-membered sugar ring molecule, β-cyclodextrin of 7-membered sugar ring molecule or γ-cyclodextrin of 8-membered sugar ring molecule, and preferably β-cyclodextrin.

Figure 4:
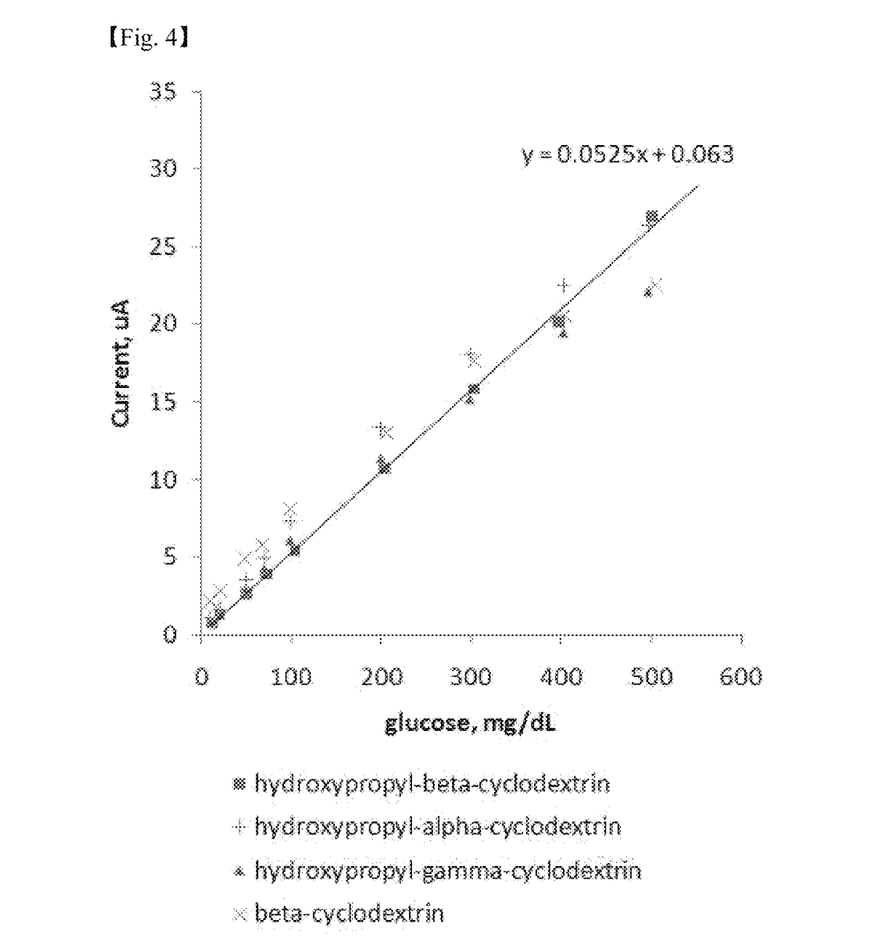
FIG. 4 is a graph showing the current changes caused by the various glucose concentrations with using the face-to-face biosensor in Example 1 of the present invention.

The derivatives of the cyclodextrins can be the cyclodextrins containing at least a functional group selected from the group consisting of hydropropyl, methyl and the like. For example, the representative derivatives of the cyclodextrins are hydroxypropyl-α-cyclodextrin, hydroxypropyl-β-cyclodextrin, hydroxypropyl-γ-cyclodextrin, methyl-β-cyclodextrin and the like. Hydroxypropyl-β-cyclodextrin can be presented as an example, but the derivatives of α-cyclodextrin and γ-cyclodextrin shows the similar properties to the hydroxypropyl-β-cyclodextrin (FIG. 4).

The hydrophilic inclusion compounds including cyclodextrins and derivatives of the cyclodextrins, specifically hydroxypropyl-β-cyclodextrin are high water-solubility and can increase the solubility and stability of the reagent by forming water-soluble and stable complex with poorly-soluble materials in the reagent, when the hydrophilic inclusion compounds are contained in a reagent composition for redox reaction, specifically a reagent composition useful for an electrochemical biosensor.

In the present invention, the hydrophilic inclusion compound is provided for stabilizing a reagent for redox reaction, for example a reagent composition useful for an electrochemical biosensor. As an embodiment, there is provided a reagent for redox reaction stabilizing composition including the hydrophilic inclusion compound as an active component, or a stabilizing agent of the reagent used for biosensor.

The reagent for redox reaction or the reagent composition useful for an electrochemical biosensor with an increased stability can be the reagent for redox reaction or the reagent composition useful for an electrochemical biosensor including oxidoreductase and electron-transfer mediator.

In another embodiment, there is provided a reagent for redox reaction or a reagent composition being useful for an electrochemical biosensor with an increased stability, including oxidoreductase, electron-transfer mediator and hydrophilic inclusion compound. More specifically, the reagent composition for redox reaction can be applied for a reagent composition for electrochemical biosensor. Thus, a reagent composition for electrochemical biosensor with an increased stability can be provided.

In further embodiment, a method of preparing a reagent for redox reaction with increased stability includes a step of mixing an oxidoreductase, an electron-transfer mediator and a hydrophilic inclusion compound. Specifically, the reagent composition for redox reaction can be applied for the electrochemical biosensor, and thus a method of preparing a reagent for redox reaction being useful for electrochemical biosensor with increased stability includes a step of mixing an oxidoreductase, an electron-transfer mediator and a hydrophilic inclusion compound. In the method, the step of mixing oxidoreductase, electron-transfer mediator and hydrophilic inclusion compound can be performed by mixing an oxidoreductase and an electron-transfer mediator, and adding a hydrophilic inclusion compound to the mixture.

An embodiment provides an electrochemical biosensor including a reagent composition for electrochemical biosensor with increased stability.

A further embodiment provides an electrochemical biosensor including a reagent composition for electrochemical biosensor with increased stability.

As described above, the hydrophilic inclusion compound can stabilize the reagent.

Unless otherwise specified herein, a reagent with increased stability including oxidoreductase, electron-transfer mediator and a hydrophilic inclusion compound used as a stabilizer for the reagent is described as 'a reagent composition for redox reaction or a reagent composition for electrochemical biosensor', and is described differently from a conventional reagent including oxidoreductase and electron-transfer mediator which is referred to as 'a reagent for redox reaction or a reagent applied for the electrochemical biosensor'. Also, unless otherwise specified herein, the term 'a reagent composition' can include the reagent composition for redox reaction or a reagent composition for electrochemical biosensor.

The oxidoreductase is a generic term of an enzyme catalyzing the redox reaction in a living organism, and specifically can be an enzyme being reduced by reacting with the subject metabolite to be detected. The reduced enzyme reacts with the electron-transfer mediator, thereby producing a signal such as current change, which can be detected for measuring the metabolite quantitatively. The examples of oxidoreductases being useful for the present invention can be at least one selected from the group consisting of various dehydrogenases, oxidases, esterases and the like. Depending upon the redox reaction type and the subject material to be detected, a suitable enzyme can be selected and used among the enzymes.

Concretely, the oxidoreductase can be at least one selected from the group consisting of glucose dehydrogenase, glutamate dehydrogenase, glucose oxidase, cholesterol oxidase, cholesterol esterase, lactate oxidase, ascorbic acid oxidase, alcohol oxidase, alcohol dehydrogenase, bilirubin oxidase and the like.

The reagent composition can further include a cofactor storing hydrogen which is obtained from the subject material to be detected, for example the metabolites by using the oxidoreductase. The examples of cofactor can be at least one selected from the group consisting of flavin adenine dinucleotide (FAD), nicotinamide adenine dinucleotide (NAD), Pyrroloquinoline quinone (PQQ) and the like.

For example, to measure the blood glucose concentration, the oxidoreductase can be glucose dehydrogenase (GDH) and the cofactor of glucose dehydrogenase can be flavin adenine dinucleotide-glucose dehydrogenase (FAD-GDH), and/or nicotinamide adenine dinucleotide-glucose dehydrogenase.

In a specific example, the oxidoreductase can be FAD-GDH (for example, EC 1.1.99.10 etc.), NAD-GDH (for example, EC 1.1.1.47 etc.), PQQ-GDH (for example, EC1.1.5.2 etc.), glutamic acid dehydrogenase (for example, EC 1.4.1.2 etc.), glucose oxidase (for example, EC 1.1.3.4 etc.), cholesterol oxidase (for example, EC 1.1.3.6 etc.), cholesterol esterase (for example, EC 3.1.1.13 etc.), lactate oxidase (for example, EC 1.1.3.2 etc.), ascorbic acid oxidase (for example, EC 1.10.3.3 etc.), alcohol oxidase (for example, EC 1.1.3.13 etc.), alcohol dehydrogenase (for example, EC 1.1.1.1 etc.), bilirubin oxidase (for example, EC 1.3.3.5 etc.) and etc.

After electron-transfer mediator reacts with the reduced enzyme produced from the reaction with the metabolite to be detected, the reduced electron-transfer mediator can produce the current in electrode surface applied with the redox potential.

The electron-transfer mediator can be a mixture of a first electron-transfer mediator and a second electron-transfer mediator.

Figure 6:
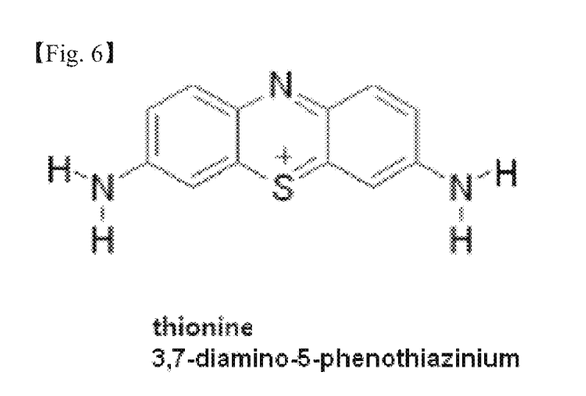
FIG. 6 is the structure of thionine used an embodiment of the present invention.
Figure 7:
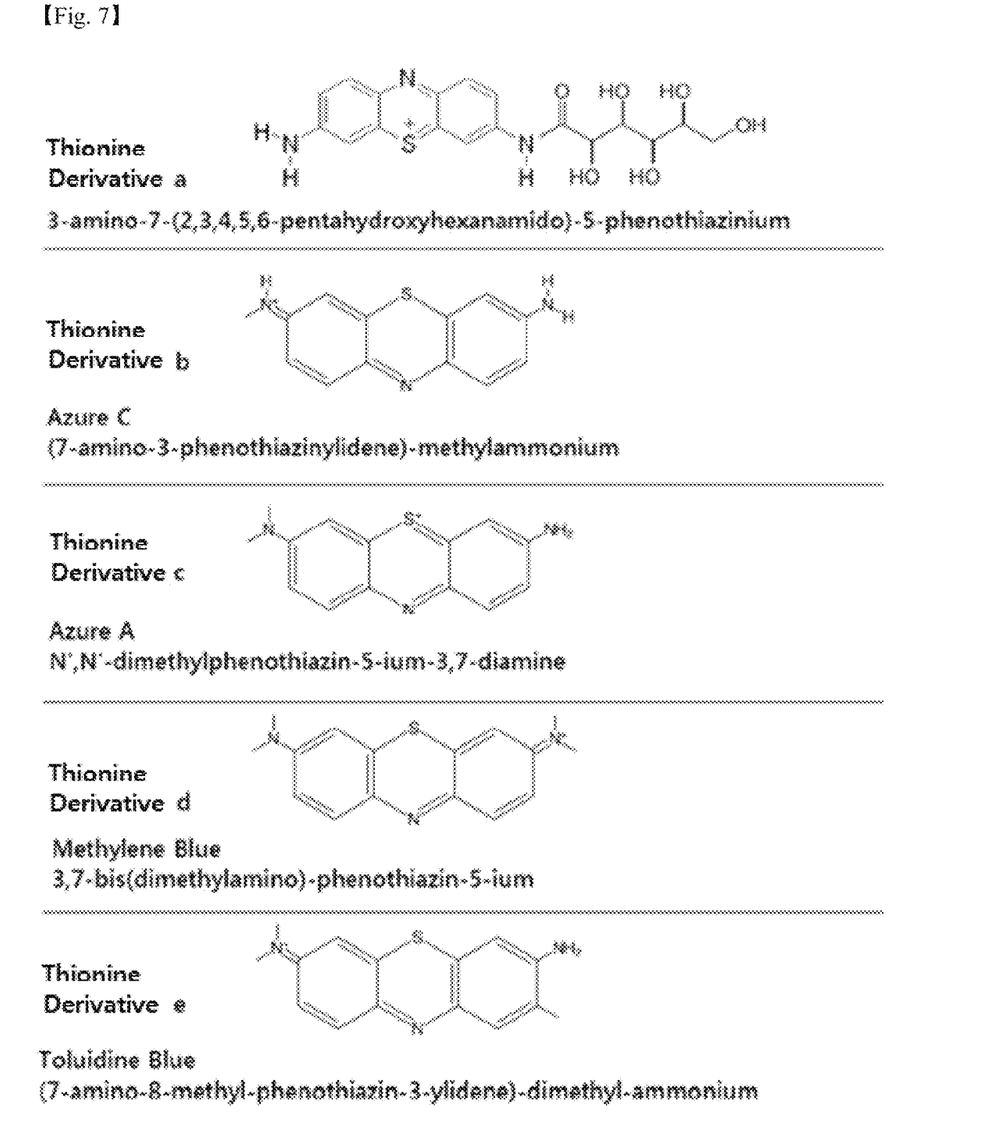
FIG. 7 is the structure of thionine derivative used an embodiment of the present invention.

In the mixture of the first electron-transfer mediator and the second electron-transfer mediator, the first electron-transfer mediator can be a metal-containing complex, and the second electron-transfer mediator can be at least one selected from the group consisting of thionine, 1-methoxy PMS (1-Methoxy-5-methylphenazinium methylsulfate), 3-amino-7-(2,3,4,5,6-pentahydroxy hexanamido)-5-phenothiazinium, 1-Methoxy-5-methylphenazinium, Azure C, Azure A, Methylene Blue, Toluidine Blue, and the derivatives thereof (FIG. 6 and FIG. 7). The metal-containing complex can be at least one selected from the group consisting of Ru, Fe, Os, Rh, Mo, and Ir.

In an embodiment, the metal-containing complex can be at least one selected from the group consisting of ruthenium complex, for example hexaammonium ruthenium chloride

[Ru(NH$_3$)$_6$Cl$_3$], ruthenium triphendione {[Ru(phendione)$_3$]$^{2+}$, phendione=1,10-phenanthroline-5,6-dione}, ruthenium tpybpy {[Ru(tpy)(bpy)H$_2$O]$^{2+}$, tpy=2,2':6',2''-terpyridine, bpy=2,2'-bipyridine} and the like.

As the electron-transfer mediator, in case of a mixture of thionine or derivatives thereof in combination with the metal-containing complex, and/or a mixture of 1-methoxy PMS or derivatives thereof in combination with the metal-containing complex, a molar ratio of thionine or 1-methoxy PMS and metal-containing complex can be 1:1 to 20 (mole of thionine or 1-methoxy PMS: mole of metal-containing complex), or more specifically 1:1 to 10.

According to a preferred example, the ruthenium complex can be used together thionine or its derivative as an electron-transfer mediator, thereby notably increasing the glucose detection capacity, and removing the effect of various materials disturbing the glucose detection.

The reagent composition including metal-containing complex (for example, ruthenium complex) and thionine or thionine derivative as the electron-transfer mediator, can contain metal-containing complex at an amount of 20 to 700 parts by weight, for example 60 to 700 parts by weight or 30 to 340 parts by weight, based on 100 parts by weight of oxidoreductase. The amount of the metal-containing complex can be adjusted depending on the activity of oxidoreductase. When the oxidoreductase with high activity is used in the reagent composition, the low amount metal-containing complex can achieve the desired object of the reagent composition. In general, as the activity of oxidoreductase is high, the amount of metal-containing complex can be adjusted at a low amount relatively. For example, in case of the oxidoreductase with 700 U/mg, the metal-containing complex can be used at an amount of 60 to 700 parts by weight, for example 30 to 340 parts by weight, based on 100 parts by weight of oxidoreductase. When the activity of oxidoreductase is higher than 700 U/mg, the amount of metal-containing complex can be adjusted to be lower value. When the amount of metal-containing complex is lower than the range, the reactivity of sensor becomes low at a high blood glucose level, and when the amount exceeds the range, the dissolution rate of the reagent is very low.

In a reagent composition including metal-containing complex (for example, ruthenium complex) and thionine or its derivative as the electron-transfer mediator, the thionine or its derivative can be included at an amount of 2 to 25 parts by weight, for example 6 to 25 parts by weight or 6 to 20 parts by weight, based on 100 parts by weight of oxidoreductase. The amount of thionine or its derivative can be adjusted suitably by considering the activity of oxidoreductase. When the activity of oxidoreductase is high, a small amount of metal-containing complex can achieve the effect of reagent composition. As the activity of oxidoreductase is higher, the amount of thionine or its derivative can be adjusted to be a small amount. For example, when the oxidoreductase with an activity of 700 U/mg is used, the thionine or its derivative can be included at an amount of 6 to 25 parts by weight or 6 to 20 parts by weight.

When the oxidoreductase has an activity higher than 700 U/mg, the amount of thionine or its derivative can be adjusted to be a smaller amount. If the amount of thionine or its derivative is less than the ranges, the sensor is insensitive to the high blood glucose concentration. If the amount is higher than the ranges, the reagent cannot be dissolved in blood rapidly.

The reagent composition can include hydrophilic inclusion compound as a reagent stabilizer at an amount of 50 to 600 parts by weight, for example 80 to 500 parts by weight, 100 to 450 parts by weight, 200 to 600 parts by weight, 300 to 500 parts by weight, or 350 to 450 parts by weight, based on 100 parts by weight of oxidoreductase. For example, when using oxidoreductase with an activity of 700 U/mg, the hydrophilic inclusion compound can be used at an amount of 200 to 600 parts by weight, specifically 300 to 500 parts by weight, or more specifically 350 to 450 parts by weight based on 100 parts by weight of oxidoreductase. If the activity of oxidoreductase is higher than 700 U/mg, the amount of inclusion compound can be adjusted to be lower amount. When the hydrophilic inclusion compound used as the reagent stabilizer is less than the ranges, the thionine or its thionine derivative cannot be dissolved completely. If the amount of hydrophilic inclusion compound is higher than the range, the sensitivity of sensor may become low. Thus, the amount of hydrophilic inclusion compound can be preferably, when the amount is used with the ranges.

The reagent composition can further include at least an additive selected from the group consisting of surfactant, water-soluble polymer, tertiary ammonium salt, fatty acids, thickening agent and etc. as a dispersant in the reagent dissolution, an adhesive in the reagent preparation, and/or a long-term stabilizer.

The surfactant can make the reagent be distributed and coated on an electrode in uniform thickness. The examples of surfactant include at least one selected from the group consisting of TRITON X-100 (4-(1,1,3,3-Tetramethylbutyl)phenyl-polyethylene glycol), sodium dodecyl sulfate, perfluorooctane sulphonate, sodium stearate and etc. The reagent composition of the present invention can the surfactant at an amount of 3 to 25 parts by weight, for example 10 to 25 parts by weight with respect to 100 parts by weight of oxidoreductase, in order that the reagent can be spread evenly on the electrode and coated in an uniform thickness. For example, when the oxidoreductase with an activity of 700 U/mg is used, the surfactant can be included at an amount of 10 to 25 parts by weight. When the activity of oxidoreductase is higher than, the amount of surfactant can be adjusted to be lower amount than the range.

The water-soluble polymer helps to make the enzyme be stable and dispersed. The water-soluble polymer can be at least one selected from the group consisting of polyvinyl pyrrolidone (PVP), polyvinyl alcohol (PVA), perfluorosulphonate), hydroxyl ethyl cellulose (HEC), hydroxypropyl cellulose (HPC), carboxymethyl cellulose (CMC), cellulose acetate, polyamide and etc. The reagent composition of the present invention can include water-soluble polymer at an amount of 10 to 70 parts by weight, for example 30 to 70 parts by weight with respect to 100 parts by weight of oxidoreductase, in order to sufficiently show the function of water-soluble polymer as a stabilizing and dispersing agent. For example, when the oxidoreductase with an activity of 700 U/mg is used, the water-soluble polymer can be included at an amount of 30 to 70 parts by weight. When the activity of oxidoreductase is higher than, the amount of water-soluble polymer can be adjusted to be lower amount than the range.

In order that the water-soluble polymer help to make the support and the enzyme be stable and dispersed, the water-soluble polymer can have a weight-average molecular weight of about 2,500 to 3,000,000, for example, about 5,000 to 1,000,000.

The tertiary ammonium salt can reduce the measurement error of the hematocrit amount. The tertiary ammonium salt can be at least one selected from the group consisting of cyltrimethyl ammonium, myristyltrimethyl ammonium, cetyltrimethyl ammonium, octadecyltrimethyl ammonium, tetrahexyl ammonium and etc. In order that the tertiary ammonium salt can reduce the measurement error of the hematocrit amount, the reagent composition of present invention can include the tertiary ammonium salt at an amount of 20 to 130 parts by weight, for example 70 to 130 parts by weight with respect to 100 parts by weight of oxidoreductase. For example, when the oxidoreductase with an activity of 700 U/mg is used, the tertiary ammonium salt can be included at an amount of 70 to 130 parts by weight. When the activity of oxidoreductase is higher than, the amount of the tertiary ammonium salt can be adjusted to be lower amount than the range.

Like the tertiary ammonium salt, the fatty acids can reduce the measurement error of the hematocrit amount, and expand the linear dynamic range of biosensor at a high concentration. The fatty acids can be at least one selected from the group consisting of a fatty acid having a carbon chain of $C_4$~$C_{20}$ and its salts, or preferably a fatty acid having a carbon chain of $C_6$~$C_{12}$ and its salts. The examples of fatty acids include at least one selected from the group consisting of caproic acid, heptanic acid, caprylic acid, octanoic acid, nonanoic acid, capric acid, undecanoic acid, lauric acid, tridecanoic acid, myristic acid, pentadecanoic acid, palmitic acid, heptadecanoic acid, stearic acid, non-adecanoic acid, arachidonic acid and fatty acids thereof. In order that the fatty acids can reduce the measurement error of the hematocrit amount, and expand the linear dynamic range of biosensor at a high concentration, the reagent composition of present invention can include the fatty acids at an amount of 10 to 70 parts by weight, for example 30 to 70 parts by weight based on 100 parts by weight of oxidoreductase. For example, when the oxidoreductase with an activity of 700 U/mg is used, the fatty acid can be included at an amount of 30 to 70 parts by weight. When the activity of oxidoreductase is higher than 700 U/mg, the amount of the fatty acid can be adjusted to be lower than the range.

The thickening agent can make the reagent adhere to electrode strongly. The thickening agent includes at least one selected from the group consisting of hydroxyethyl cellulose (NATROSOL), DEAE-Dextran hydrochloride and etc. To fix strongly the reagent to the electrode, the reagent composition of the present invention can include the thickening agent at an amount of 10 to 90 parts by weight, for example 30 to 90 parts by weight, based on 100 parts by weight of oxidoreductase. For example, when using oxidoreductase with an activity of 700 U/mg, the thickening agent can be used at 30 to 90 parts by weight, based on 100 parts by weight of oxidoreductase. When using oxidoreductase with higher activity than 700 U/mg, the amount of thickening agent can be adjusted to be lower amount.

An embodiment of the present invention provides an electrochemical biosensor including the reagent composition.

Figure 1:
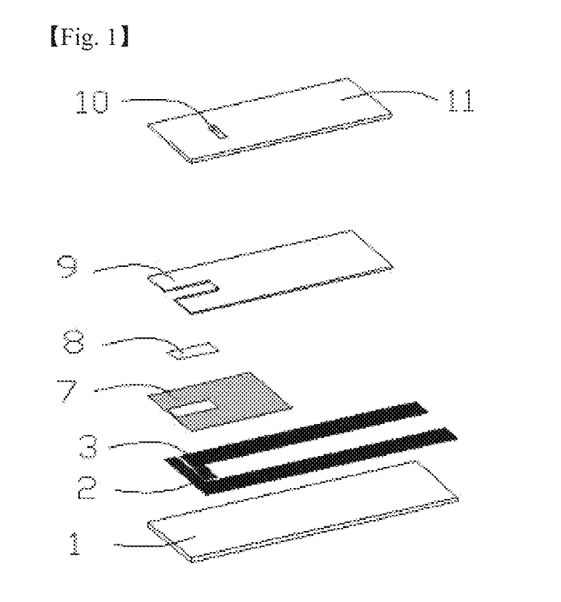
FIG. 1 is an exploded skew drawing of planar-type biosensor in accordance with an embodiment of the present invention.

An embodiment provides a planar-type electrochemical biosensor including a working electrode and an auxiliary electrode located on the same plane in which the reagent composition of present invention is contained on the working electrode (FIG. 1).

Figure 2:
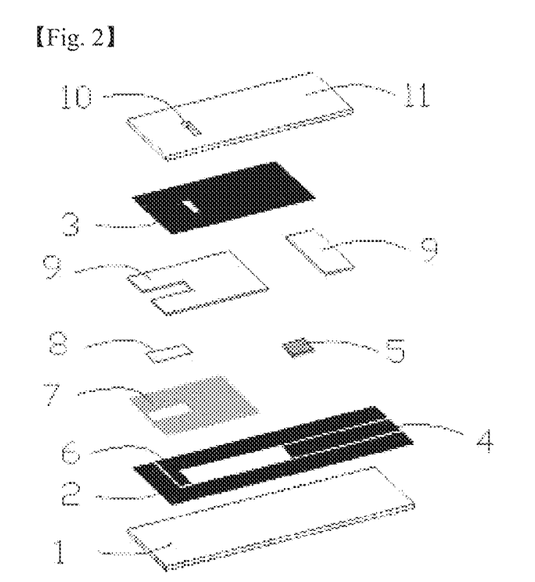
FIG. 2 is an exploded skew drawing of face-to-face (sandwich-type) biosensor in accordance with an embodiment of the present invention.

Another embodiment provides a face-to-face type electrochemical biosensor including a working electrode and an auxiliary electrode located on the different plane in which the reagent composition of present invention is contained on the working electrode (FIG. 2).

In the biosensor, the reagent composition can be included at any shape, specifically in a coated layer of working electrode, but not limited thereto.

The planar-type and face-to-face type electrochemical biosensor can be manufactured according to the methods disclosed in the prior art such as KR10-2004-0105429, KR10-2006-0089464, KR10-0854389, KR10-2008-0080841, KR10-2008-0084030, KR10-2008-0088028 and etc.

Hereinafter, the structures of the planar-type and face-to-face type electrochemical biosensor are explained by referring to FIG. 1 and FIG. 2.

The planar-type electrochemical biosensor in FIG. 1 includes a working electrode and an auxiliary electrode located on the same plane. From the top to the bottom direction, upper plate 11 equipped with air-discharging air outlet 10 for making the blood spread into the sensor; middle plate 9 adhering the upper plate and the lower plate by using the adhesive layers on both sides and making blood spread into the electrode due to the blood capillarity; a reagent composition 8 of present invention contained in the working electrode and auxiliary electrode (counter electrode), for example by coating; an insulating plate 7 equipped the channel part for defining the areas of working electrode and auxiliary electrode; the working electrode 2 and the auxiliary electrode on the lower plate 3; and a lower plate 1 where the working electrode and the auxiliary electrode are formed, are sequentially stacked structure.

The face-to-face type electrochemical biosensor in FIG. 2 includes a working electrode and an auxiliary electrode on the different plane. From the top to the bottom direction, a upper plate 11 equipped with air outlet 10 for making the blood spread into the sensor and an auxiliary electrode printed thereon; an auxiliary electrode 3 printed on the upper plate; middle plate 9 adhering the upper plate and the lower plate by using the adhesive layers on both sides and making blood spread into the electrode due to the blood capillarity; a reagent composition 8 of present invention contained in the working; an insulating plate 7 equipped the channel part for defining the areas of working electrode and auxiliary electrode; working electrode 2 printed on the lower plate; a lead 4 of auxiliary electrode; flow-sensing electrode 6 for detecting the blood input rate; and a lower plant 1 where the working electrode, the lead of auxiliary electrode and the flow-sensing electrode are formed, are sequentially stacked structure.

As described above, the reagent composition of present invention after the sensor is stored in a long time, the capacity of sensor is not nearly changed for detecting the subject material, such as glucose. Thus, it can be useful for an electrochemical biosensor detecting glucose concentration.

Hereinafter, the present invention will be described referring to the following examples. However, these examples are merely illustrative of the present invention, the scope of which shall not be limited thereto.

EXAMPLE

Example 1

Preparation of a Reagent Composition Including a Reagent Stabilizer

In addition to 100 parts by weight of oxidoreductase of adenine dinucleotide-glucose dehydrogenase, FAD-GDH, EC 1.1.99.10);

80 parts by weight (50 mM) of $Ru(NH_3)_6Cl_3$) as a metal-containing complex; 36 parts by weight (20 mM) of thionine; 406 parts by weight (50 mM) of hydroxypropyl- β-cyclodextrin; 52 parts by weight of sodium octanoate as fatty acid; 104.3 parts by weight of myristyltrimethylammonium bromide as a tertiary ammonium salt; 52 parts by weight of DEAE-Dextran hydrochloride and 11.7 parts by weight of NATROSOL(hydroxyethyl cellulose) as a thickening agent; 52 parts by weight of 80%-hydrogenated Polyvinyl alcohol (weight-average molecular weight: 9,000~10,000) as a water-soluble polymer; and 17.4 parts by weight of surfactant (TRITON X-100 (4-(1,1,3,3-Tetramethylbutyl) phenyl-polyethylene glycol)) were dissolved in sodium phosphate buffer solution (pH 6.4, 0.1 M, 1249 ml) and deionized water (1614.6 ml), and filtered to remove the remaining particles, to obtain the reagent composition for redox reaction.

Example 2

Planar-Type Biosensor Including a Reagent Composition of Example 1

The planar-type biosensor equipped with a feeding part of mean value 0.5 μl was manufactured as shown in FIG. 1:

a lower polyester plate 1 includes the working electrode (area: 1.05 $mm^2$) and auxiliary electrode formed thereon, a working electrode 2 and an auxiliary electrode 3 refer to the electrodes which were prepared by printing carbon-graphite according to the screen printing method an insulating plate 7 for defining the areas of working electrode and auxiliary electrode, a reagent composition 8 obtained in Example 1 for coating the working electrode, a middle plate 9 with 0.10 mm thickness, adhering the upper plate and the lower plate by using the adhesive layers on both sides and making blood spread into the electrode due to the blood capillarity, an air outlet 10 for making the blood spread into the sensor, and an upper polyester plate 11 consisting of biosensor.

Example 3

Face-to-Face Type Biosensor Including a Reagent Composition of Example 1

In an example of face-to-face type biosensor example shown in FIG. 2, the face-to-face type biosensor having sample feeding part of mean value 0.5 μl was manufactured.

The biosensor of FIG. 2 is explained as follows:

a polyester lower plate 1 which the working electrode (are: 1.95 $mm^2$), lead of auxiliary electrode and flow-sensing electrode are printed thereon according to the screen printing method, electrodes 2, 3, 4 and 6, which are prepared by printing according to the screen printing method (working electrode 2, auxiliary electrode 3, lead of auxiliary electrode 4, flow-sensing electrode 6 detecting the input rate of blood), a circuit connecting part (Ag/AgCl) 5, connecting a lead of auxiliary electrode 4 and auxiliary electrode 3, an insulating plate 7 for defining the area of working electrode, the reagent composition 8 obtained in Example 1 for coating the working electrode, a middle plate 9 in thickness of 0.07 mm, adhering the upper plate and the lower plate by using the adhesive layers on both sides and making blood spread into the electrode due to the blood capillarity 10 is air outlet, and an upper plate 11 where the auxiliary electrode is printed thereon, to form the sensor.

Comparative Example 1

Preparation of a Reagent Composition without a Reagent Stabilizer

The reagent composition was prepared according to the same method of Example 1, except that hydroxypropyl-β-cyclodextrin as a reagent stabilizer was not used.

Comparative Example 2

Face-to-Face Type Biosensor Including a Reagent Composition of Comparative Example 1

According to the same method of Example 1-2, the face-to-face type biosensor was manufactured, except that the reagent composition of Comparative Example 1 was coated on the working electrode.

Experimental Example 1

Measurement for Current Change of Planar-Type Biosensor by Using the Standard Glucose Solution The current of glucose standard solution was measured by using the planar-type biosensor of Example 2. The glucose standard solution meant the blood samples with various glucose concentrations which were prepared by extracting blood from vein and using with glucose analyzer (manufacturer: YSI, model: 2300 Stat Plus), with adjusting the hematocrit of 42%.

Specifically, when the standard solutions each glucose concentration of 11, 22, 50, 67, 101, 202, 301, 396 or 509 mg/dL were covered on the working electrode and the auxiliary electrode simultaneously, the working electrode was applied by voltage of 0 mV for 3 seconds and by voltage 200 mV for 1 second. Then, the current was measured at 10 times for every concentration, and the mean value of measured current value was shown in FIG. 3.

Figure 3:
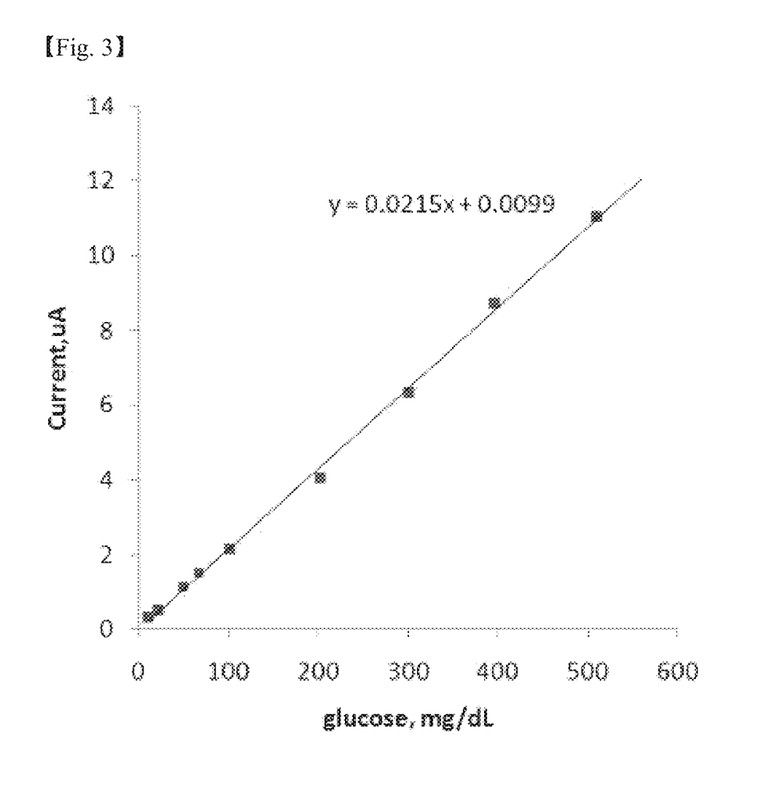
FIG. 3 is a graph showing the current changes caused by the various glucose concentration with using the planar-type biosensor in Example 2 of the present invention.

As shown in FIG. 3, the planar-type biosensor of Example 2 represented the good linearity of the increased current values as the glucose concentration increased. The slope of current value per unit area of working electrode was 20.5 nA/(mg/dL)/$mm^2$.

Experimental Example 2

Measurement of Current Changes of Face-to-Face Type Biosensor

According to the same method of Experimental Example 1, the current of glucose standard solution was measured by using the face-to-face type biosensor of Example 3, except that each glucose concentration was 11, 21, 50, 72, 104, 204, 303, 397 or 500 mg/dL.

In this example, hydroxypropyl-alpha-cyclodextrin, hydroxypropyl-beta-cyclodextrin, and hydroxypropyl-gamma-cyclodextrin were used as a reagent stabilizer instead of HP-β-CD for preparing the reagent composition according to the same method of Example 1. The biosensor was manufactured by using the reagent composition according to the same method of Example 3, and was used. The current was measured at 10 times for every concentration, and the mean value of measured current value was shown in FIG. 4.

As shown in FIG. 4, the biosensor using the reagent composition including hydroxypropyl-beta-cyclodextrin as a reagent stabilizer represented the best linearity. The slope of current value per unit area of working electrode was 26.9 nA/(mg/dL)/mm². Other biosensor using the other reagent compositions showed the good linearity also.

Experimental Example 3

Measurement of Current Changes of Face-to-Face Type Biosensor Incubated at 50° C.

To make the sensor be commercialized, the performance change of sensor must be minimized in a validation time. Experimental Example 3 test the performance stability, in case that the sensor is stored in a long time. Specifically, the face-to-face type biosensors of Example 3 and Comparative Example 2 were incubated at 50° C. for 4, 11, 17, 24, 29, 36, and 43 days and then the current of glucose standard solution was measured according to the same method of Experimental Example 2, to represent the result in FIG. 5. In the case that the sensor was stored at 50° C. for 43 days, it corresponds to the case of storage at a room temperature for 17 months.

Figure 5:
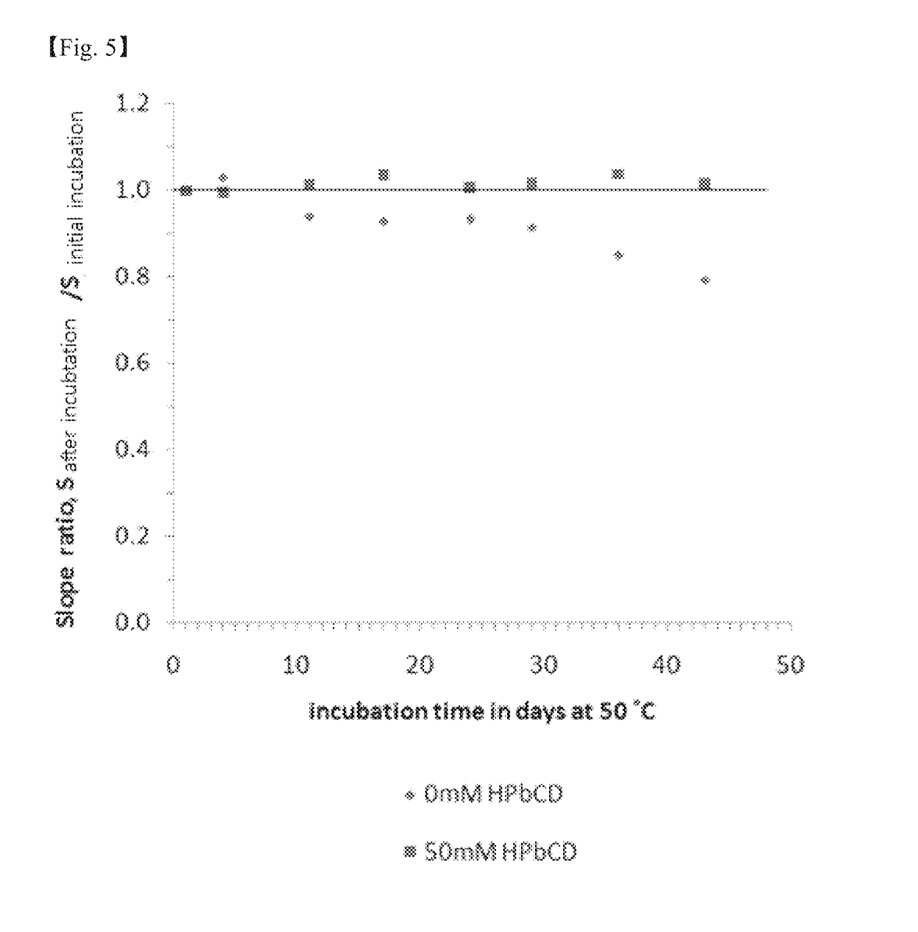
FIG. 5 is a graph showing the slope change when incubating the face-to-face biosensor of Example 3 and Comparative Example 2 at 50° C. and applying various glucose concentrations in accordance with Example 3 of the present invention.

As shown in FIG. 5, the sensor including HP-β-CD as a reagent stabilizer represented maximum slope of 3.6% for the storage time of at least 43 days. The sensor without including HP-β-CD showed the decreased slope to be 21% after 43 days storage, as the storage time passed. Thus, when HP-β-CD was added to the reagent composition, it could make the sensor be stored in a long time without changing the performance change.

The reagent composition for redox reaction including HP-β-CD showed the high stability in a long storage time, and thus was useful for a biosensor to detecting the blood glucose. The reagent composition and the composition ratio in the examples is represented by only examples, and can be freely modified or changed to adjust the sensitivity required for specific the use or performance.

What is claimed is:

1. A reagent composition for redox reaction comprising an oxidoreductase, an electron-transfer mediator, and hydroxypropyl-β-cyclodextrin as a hydrophilic inclusion compound, wherein the electron-transfer mediator is a mixture of a first electron-transfer mediator and a second electron-transfer mediator, the first electron-transfer mediator is $Ru(NH_3)_6Cl_3$, and the second electron-transfer mediator is thionine.

2. The reagent composition for redox reaction of claim 1, wherein the oxidoreductase is at least one selected from the group consisting of dehydrogenase, oxidase and esterase; or a mixture of at least an oxidoreductase selected from the group consisting of dehydrogenase, oxidase and esterase, and at least a co-factor selected from the group consisting of flavin adenine dinucleotide (FAD), nicotinamide adenine dinucleotide (NAD) and Pyrroloquinoline quinone (PQQ).

3. The reagent composition for redox reaction of claim 2, wherein the at least one selected from the group consisting of dehydrogenase, oxidase and esterase is selected from the group consisting of glucose dehydrogenase, glutamate dehydrogenase, glucose oxidase, cholesterol oxidase, cholesterol esterase, lactate oxidase, ascorbic acid oxidase, alcohol oxidase, alcohol dehydrogenase, and bilirubin oxidase.

4. The reagent composition for redox reaction of claim 2, wherein the mixture of at least an oxidoreductase selected from the group consisting of dehydrogenase, oxidase and esterase, and at least a co-factor selected from the group consisting of flavin adenine dinucleotide (FAD), nicotinamide adenine dinucleotide(NAD) and Pyrroloquinoline quinone (PQQ) oxidoreductase is at least one selected from the group consisting of flavin adenine dinucleotide-glucose dehydrogenase (FAD-GDH), and nicotinamide adenine dinucleotide-glucose dehydrogenase.

5. The reagent composition for redox reaction of claim 1, wherein the reagent composition further comprises at least an additive selected from the group consisting of surfactant, water-soluble polymer, tertiary ammonium salt, fatty acids, and thickening agent.

6. The reagent composition for redox reaction of claim 5, wherein the surfactant is at least one selected from the group consisting of TRITON X-100 (4-(1,1,3,3-Tetramethylbutyl)phenyl-polyethylene glycol), sodium dodecyl sulfate, perfluorooctane sulfonate, and sodium stearate;
the water-soluble polymer is at least one selected from the group consisting of polyvinyl pyrrolidone (PVP), polyvinyl alcohol (PVA), perfluoro sulfonate, hydroxyethyl cellulose (HEC), hydroxypropyl cellulose (HPC), carboxy methyl cellulose (CMC), cellulose acetate, and polyamide;
the tertiary ammonium salt is at least one selected from the group consisting of ecyltrimethyl ammonium, myristyltrimethyl ammonium, cetyltrimethyl ammonium, octadecyltrimethyl ammonium, and tetrahexyl ammonium; and
the fatty acid is at least one selected from the group consisting of fatty acids having carbon chain of $C_4$~$C_{20}$ and fatty acid salts;
the thickening agent is at least one selected from the group consisting of hydroxyethyl cellulose (NATROSOL) and diethylaminoethyl-Dextran (DEAE-Dextran) hydrochloride.

7. The reagent composition for redox reaction of claim 1, wherein the reagent composition for redox reaction is a reagent composition used for an electrochemical biosensor.

8. The reagent composition for redox reaction of claim 4, wherein the reagent composition for redox reaction is a reagent composition used for an electrochemical biosensor.

9. The reagent composition for redox reaction of claim 5, wherein the reagent composition for redox reaction is a reagent composition used for an electrochemical biosensor.

10. The reagent composition for redox reaction of claim 6, wherein the reagent composition for redox reaction is a reagent composition used for an electrochemical biosensor.

11. A planar electrochemical biosensor, comprising a working electrode and an auxiliary electrode located in a same plate, where the working electrode comprises the reagent composition for redox reaction as set forth in claim 7.

12. A face-to-face electrochemical biosensor, comprising a working electrode and an auxiliary electrode located in different plates, where the working electrode comprises the reagent composition for redox reaction as set forth in claim 7.

13. A method of preparing a reagent composition for redox reaction comprising mixing an oxidoreductase, an electron-transfer mediator, and hydroxypropyl-β-cyclodextrin as a hydrophilic inclusion compound, wherein the electron-transfer mediator is a mixture of a first electron-transfer mediator and a second electron-transfer mediator, the first electron-transfer mediator is Ru(NH$_3$)$_6$Cl$_3$, the second electron-transfer mediator is thionine.

14. The method of claim 13, wherein the oxidoreductase is at least one selected from the group consisting of dehydrogenase, oxidase, and esterase; or the oxidoreductase comprises a mixture of at least one selected from the group consisting of dehydrogenase, oxidase and esterase, and at least one co-factor selected from the group consisting of flavin adenine dinucleotide (FAD), nicotinamide adenine dinucleotide (NAD), and Pyrroloquinoline quinone (PQQ).

* * * * *